United States Patent [19]

Lapidus et al.

[11] Patent Number: 6,020,137
[45] Date of Patent: *Feb. 1, 2000

[54] METHODS FOR THE DETECTION OF LOSS OF HETEROZYGOSITY

[75] Inventors: Stanley N. Lapidus, Bedford, N.H.; Anthony P. Shuber, Milford, Mass.

[73] Assignee: Exact Laboratories, Inc., Maynard, Mass.

[*] Notice: This patent is subject to a terminal disclaimer.

[21] Appl. No.: 09/198,091

[22] Filed: Nov. 23, 1998

Related U.S. Application Data

[63] Continuation-in-part of application No. 08/876,857, Jun. 16, 1997, Pat. No. 5,928,870, which is a continuation-in-part of application No. 08/700,583, Aug. 14, 1996, Pat. No. 5,670,325.

[51] Int. Cl.[7] ...................................................... C12Q 1/68
[52] U.S. Cl. .............................................. 435/6; 536/24.3
[58] Field of Search ................................. 435/6; 536/24.3

[56] References Cited

U.S. PATENT DOCUMENTS

| | | |
|---|---|---|
| 4,101,279 | 7/1978 | Aslam . |
| 4,309,782 | 1/1982 | Paulin . |
| 4,333,734 | 6/1982 | Fleisher . |
| 4,445,235 | 5/1984 | Slover et al. . |
| 4,535,058 | 8/1985 | Weinberg et al. . |
| 4,683,195 | 7/1987 | Mullis et al. . |
| 4,705,050 | 11/1987 | Markham . |
| 4,735,905 | 4/1988 | Parker . |
| 4,786,718 | 11/1988 | Weinberg et al. . |
| 4,857,300 | 8/1989 | Maksem . |
| 4,871,838 | 10/1989 | Bos et al. . |
| 4,981,783 | 1/1991 | Augenlicht . |
| 4,982,615 | 1/1991 | Sultan et al. . |
| 5,087,617 | 2/1992 | Smith . |
| 5,126,239 | 6/1992 | Livak et al. . |
| 5,137,806 | 8/1992 | LeMaistre et al. . |
| 5,149,506 | 9/1992 | Skiba et al. . |
| 5,196,167 | 3/1993 | Guadagno et al. . |
| 5,248,671 | 9/1993 | Smith . |
| 5,272,057 | 12/1993 | Smulson et al. . |
| 5,302,509 | 4/1994 | Cheeseman . |
| 5,330,892 | 7/1994 | Vogelstein et al. . |
| 5,331,973 | 7/1994 | Fiedler et al. . |
| 5,348,855 | 9/1994 | Dattagupta et al. . |
| 5,352,775 | 10/1994 | Albertsen et al. . |
| 5,362,623 | 11/1994 | Vogelstein et al. . |
| 5,369,004 | 11/1994 | Polymeropoulos et al. . |
| 5,378,602 | 1/1995 | Polymeropoulos et al. . |
| 5,380,645 | 1/1995 | Vogelstein . |
| 5,380,647 | 1/1995 | Bahar . |
| 5,382,510 | 1/1995 | Levine et al. . |
| 5,409,586 | 4/1995 | Kamahori et al. . |
| 5,458,761 | 10/1995 | Kamahori et al. . |
| 5,463,782 | 11/1995 | Carlson et al. . |
| 5,466,576 | 11/1995 | Schulz et al. . |
| 5,468,610 | 11/1995 | Polymeropoulos et al. . |
| 5,468,613 | 11/1995 | Erlich et al. . |
| 5,489,508 | 2/1996 | West et al. . |
| 5,492,808 | 2/1996 | de la Chapelle et al. . |
| 5,496,470 | 3/1996 | Lenhart . |
| 5,508,164 | 4/1996 | Kausch et al. . |
| 5,512,441 | 4/1996 | Ronal . |
| 5,514,547 | 5/1996 | Balazs et al. . |
| 5,527,676 | 6/1996 | Vogelstein et al. . |
| 5,532,108 | 7/1996 | Vogelstein . |
| 5,580,729 | 12/1996 | Vogelstein . |
| 5,709,998 | 1/1998 | Kinzler et al. . |

FOREIGN PATENT DOCUMENTS

| | | |
|---|---|---|
| 11325/95 | 10/1994 | Australia . |
| 0 284 362 A2 | 9/1988 | European Pat. Off. . |
| 0 337 498 | 10/1989 | European Pat. Off. . |
| 0 390 323 A2 | 10/1990 | European Pat. Off. . |
| 0 390 323 A3 | 10/1990 | European Pat. Off. . |
| 0 407 789 A1 | 1/1991 | European Pat. Off. . |
| 0 407 789 B1 | 1/1991 | European Pat. Off. . |
| 0 608 004 A2 | 7/1994 | European Pat. Off. . |
| 0 259 031 B1 | 11/1994 | European Pat. Off. . |
| 0 664 339 A1 | 7/1995 | European Pat. Off. . |
| WO 92/13103 | 8/1992 | WIPO . |
| WO 93/18186 | 9/1993 | WIPO . |
| WO 93/20233 | 10/1993 | WIPO . |
| WO 94/00603 | 1/1994 | WIPO . |
| WO 94/09161 | 4/1994 | WIPO . |
| WO 94/10575 | 5/1994 | WIPO . |
| WO 94/11383 | 5/1994 | WIPO . |
| WO 95/07361 | 3/1995 | WIPO . |
| WO 95/09928 | 4/1995 | WIPO . |

(List continued on next page.)

OTHER PUBLICATIONS

Sanger F., S. Nicklen and A.R. Coulson (Dec. 1977) "DNA sequencing with chain–terminating inhibitors" vol. 74, No. 12 *Proc. Natl. Acad. Sci. USA* pp. 5463–5467.

Wallace R.B., et al. (1979) "Hybridization of synthetic oligodeoxyribonucleotides to Φχ 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extracting DNA from Stool Samples for Use in Hybridization Assays" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

Litia A., L. Liukkonen and H. Siitari (1992) "Simultaneous detection of two cystic fibrosis alleles using dual–label time–resolved fluorometry" vol. 6 *Molecular and Cellular Probes* pp. 505–512.

Young G. P., and B. H. Demediu (1992) "The genetics, epidemiology, and early detection of gastrointestinal cancers" vol. 4 *Current Opinion in Oncology* pp. 728–735.

Hoss M., et al. (Sep. 17, 1992) "Excrement analysis by PCR" *Scientific Correspondence* pp. 199.

*Primary Examiner*—Scott W. Houtteman
*Attorney, Agent, or Firm*—Testa, Hurwitz & Thibeault LLP

[57] ABSTRACT

Methods are provided for detecting loss of heterozygosity in a pooled nucleic acid sample obtained from a patient population. These methods are particularly useful for identifying populations or individuals within a population with gene mutations indicative of early colorectal cancer.

38 Claims, 3 Drawing Sheets

FOREIGN PATENT DOCUMENTS

| | | |
|---|---|---|
| WO 95/09929 | 4/1995 | WIPO . |
| WO 95/12606 | 5/1995 | WIPO . |
| WO 95/13397 | 5/1995 | WIPO . |
| WO 95/15400 | 6/1995 | WIPO . |
| WO 95/6792 | 6/1995 | WIPO . |
| WO 95/19448 | 7/1995 | WIPO . |
| WO 95/8818 | 7/1995 | WIPO . |
| WO 95/25813 | 9/1995 | WIPO . |
| WO 95/31728 | 11/1995 | WIPO . |
| WO 96/01907 | 1/1996 | WIPO . |
| WO 96/06951 | 3/1996 | WIPO . |
| WO 96/08514 | 3/1996 | WIPO . |
| WO 96/12821 | 5/1996 | WIPO . |
| WO 96/13611 | 5/1996 | WIPO . |

OTHER PUBLICATIONS

Sidransky, et al. (Apr. 3, 1992) "Identification of ras Oncogene Mutations in the Stool of Patients with Curable Colorectal Tumors" vol. 256 *Science* pp. 102–105.

Takeda S., S. Ichii, and Y. Nakamura (1993) "Detection of K–ras Mutation in Sputum by Mutant–Allele–Specific Amplification (MASA)" vol. 2 *Human Mutation* pp. 112–117.

Leong P. K., et al. (1993) "Detection of MYCN Gene Amplification and Deletions of Chromosome 1p in Neuroblastoma by In Situ Hybridization Using Routine Histologic Sections" vol. 69, No. 1 *Laboratory Investigations* pp. 43–50.

Thibodeau S.N., G. Bren, D. Schaid (May 7, 1993) "Microsatellite Instability in Cancer of the Proximal Colon" vol. 260, *Science* pp. 816–819.

Naber S. P.(Dec. 1, 1994) "Molecular Pathology—Detection of Neoplasia" vol. 331 *New England Journal of Medicine* pp. 1508–1510.

Cave H., et al. (1994) "Reliability of PCR Directly from Stool Samples: Usefulness of an Internal Standard" vol. 16, No. 5 *BioTechniques* pp. 809–810.

Caldas, C., et al (Jul. 1, 1994) "Detection of K–ras Mutations in the Stool of Patients with Pancreatic Adenocarcinoma and Pancreatic Ductal Hyperplasia" vol. 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Nature* pp. 215–220.

Fearon E. R.(1995) "Molecular Abnormalities in Colon and Rectal Cancer" *The Molecular Basis of Cancer*, W. B. Sauders Co., Phila., pp. 340–357.

Ravelingien N., J. C. Pector & T. Velu (1995) "Contribution of molecular oncology in the detection of colorectal carcinomas" vol. 58 *Acta Gastro–Enterologica Belgica* pp. 270–273.

Duffy M.J.(1995) "Can Molecular Markers Now Be Used for Early Diagnosis of Malignancy?" vol. 41, No. 10 *Clin. Chem.* pp. 1410–1413.

Blum H.E.(1995) "Colorectal Cancer: Future Population Screening for Early Colorectal Cancer" vol. 31A *European Journal of Cancer*, pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" vol. 191 *Path. Res. Pract.* pp. 399–402.

Smith–Ravin J., J. England, I.C. Talbot, W. Bodmer (1995) "Detection of c–Ki–ras mutations in faecal samples from sporadic colorectal cancer patients" vol. 36 *Gut* pp. 81–86.

Orlow I., et al. (Oct. 18, 1995) "Deletion of the p16 and p15 Genes in Human Bladder Tumors" vol. 87, No. 20 *Journal of the National Cancer Institute* pp. 1524–1529.

Hasegawa, Y., et al.,(1995) "Detection of K–ras mutations in DNAs isolated from feces of patients with colorectal tumors by mutant–allele–specific amplification (MASA)" vol. 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" vol. 6, *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" vol. 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., et al. (May 1996) "Identification of Subjects at Risk for Colorectal Carcinoma Through a Test Based on K–ras Determination in the Stool" vol. 110, No. 5 *gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Apr. 15, 1996) "Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplification" vol. 20, No. 5 *BioTechniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of In Vitro Amplified DNA" In *Recombinant DNA Methodology II* (Wu, ed) pp. 565–578.

Myers, R.M., "The Pulses of Subtraction", vol. 259 Science, pp. 942–943 (1993).

Jonsson et al., From Mutation mapping to phenotype cloning: vol. 92 Proc. Natl. Sci. USA, pp. 83–85 (1995).

Watson et al. "Isolation of Differentiality Expressed Sequence Tags from Human Breast Cancer" Advances in Brief vol. 54 *Cancer Research* pp. 4598–4602.

A.

B.

METHODS FOR THE DETECTION OF LOSS OF HETEROZYGOSITY

This application is a continuation-in-part of U.S. patent application Ser. No. 08/876,857, filed Aug. 16, 1997 now U.S. Pat. No. 5,928,870, which is a continuation-in-part of U.S. patent application Ser. No. 08/700,583, filed Aug. 14, 1996 (now U.S. Pat. No. 5,670,325), the disclosure of which is incorporated by reference herein.

FIELD OF THE INVENTION

This invention relates to methods useful for disease diagnosis in a sample from a patient population containing a small amount of mutated genetic material dispersed within a large amount of normal genetic material.

BACKGROUND OF THE INVENTION

Cancer is a disease characterized by genomic instability. The acquisition of genomic instability is thought to arise from a coincident disruption of genomic integrity and a loss of cell cycle control mechanisms. Generally, a disruption of genomic integrity is thought merely to increase the probability that a cell will engage in the multistep pathway leading to cancer. However, coupled with a loss of cell cycle control mechanisms, a disruption in genomic integrity may be sufficient to generate a population of genomically unstable neoplastic cells. A common genetic change characteristic of transformation is loss of heterozygosity. Loss of heterozygosity at a number of tumor suppressor genes has been implicated in tumorigenesis. For example, loss of heterozygosity at the P53 tumor suppressor locus has been correlated with various types of cancer. Ridanpaa, et al., *Path. Res. Pract*, 191: 399–402 (1995). The loss of the apc and dcc tumor suppressor genes has also been associated with tumor development. Blum, *Europ. J. Cancer*, 31A: 1369–372 (1995).

Loss of heterozygosity is therefore a potentially useful marker for detecting the early stages of cancer. However, in the early stages of cancer only a small number of cells within a tissue have undergone transformation. Genetic changes characteristic of genomic instability theoretically can serve as markers for the early stages of, for example, colon cancer, and can be detected in DNA isolated from biopsied colonic epithelium and in some cases from transformed cells shed into fecal material. Sidransky, et al., *Science*, 256: 102–105 (1992).

Detection methods proposed in the art are time-consuming and expensive. Duffy, supra. Moreover, methods according to the art cannot be used to identify a loss of heterozygosity or microsatellite instability in small sub-population of cells when the cells exist in a heterogeneous (i.e., clonally impure) sample. For example, in U.S. Pat. No. 5,527,676, it is stated that tissue samples in which a mutation is to be detected should be enriched for tumor cells in order to detect the loss of heterozygosity in a p53 gene.

Colorectal cancer is a common cause of death. Any tumor or precancerous polyp that develops along the length of the colon or the rectum sheds cells or DNA into the lumen of the colon. Shed cells or cellular DNA are usually incorporated onto and into stool as stool passes through the colon. In the early stages of cancer, cancerous or precancerous cells represent a very small fraction of the shed epithelial cells or DNA in stool. Current methods for early detection of colorectal cancer do not focus on detecting cancerous or precancerous cells in stool. Rather, such methods typically focus on extracellular indicia of the presence of cancer, such as the presence of fecal occult blood or carcinoembryonic antigen circulating in serum.

It is thought that sporadic colorectal cancers result from an accumulation of mutations in oncogenes and tumor suppressor genes. Sporadic colorectal cancer is also typically associated with massive loss of genetic material called loss of heterozygosity. Such mutations appear to occur at a point in the etiology of the disease that is much earlier than the point at which extracellular indicia or clinical signs of cancer are observed. If detected early, colon cancer may be effectively treated by surgical removal of the cancerous tissue. Surgical removal of early-stage colon cancer is usually successful because colon cancer begins in cells of the colonic epithelium and is isolated from the general circulation until the occurrence of invasion through the epithelial lining. Thus, detection of early mutations in colorectal cells would greatly increase survival rate.

Current non-invasive methods for detection of colon cancer involve the detection of fecal occult blood and carcinoembryonic antigen. These methods often either fail to detect colorectal cancer or they detect colorectal cancer only after it has progressed to a less treatable stage. Moreover, carcinoembryonic antigen is thought not to be an effective predictor of cancer but merely an indicator of recurrent cancer.

Invasive techniques, such as endoscopy, while effective, are expensive and painful and suffer from low patient compliance. Accordingly, current colon cancer screening methods are not practical for screening large segments of the population. See, e.g., Blum, *Europ. J. Cancer*, 31A: 1369–1372 (1995).

Therefore, there is a need in the art for simple and efficient non-invasive methods for reliable large-scale screening to identify individuals with early stage disease. Such methods are provided herein.

SUMMARY OF THE INVENTION

The present invention provides methods for detecting a subpopulation of genomically transformed nucleic acids. Such methods detect the presence in a biological sample of a subpopulation of nucleic acids which have a sequence different from the wild type, and from bacterial, parasitic, or contaminating organisms that may also be present in the sample. Practice of the invention permits, for example, detection of a trace amount of DNA derived from cancer or precancer cells in a biological sample containing a majority of "normal" DNA.

A sample may be derived from specimens obtained from individual patients, or from pooled specimens from a plurality of members of a population (e.g, healthy individuals, diseased individuals, heterozygotes, etc). A preferred use of methods of the invention is to reliably detect in stool samples voided by patients, the presence of a trace amount of DNA shed into the colon at the site of a symptomatic or asymptomatic precancerous or cancerous lesion. The invention takes advantage of several important insights which permit, for example, reliable detection of a DNA deletion at a known genomic site characteristic of a known cancer cell type. Methods of the invention are useful for the detection and diagnosis of a genetic abnormality, such as a loss of heterozygosity or, more generally, a mutation, which can be correlated with a disease, such as cancer. For purposes of the present invention, unless the context requires otherwise, a "mutation" includes modifications, rearrangements, deletions, substitutions, and additions in a portion of genomic DNA or its corresponding mRNA.

In general, the invention comprises methods for counting (i.e. enumerating) the number of molecules of a target genomic sequence present in a sample obtained from one patient, or in pooled samples obtained from members of a patient population. The invention further comprises methods for comparing the number of molecules with a reference number to determine whether any difference between the two numbers is statistically significant, a statistically significant difference being indicative of loss of heterozygosity involving a genomic region comprising the target sequence. A useful reference number is the number of molecules of a reference genomic sequence. The reference genomic sequence is chosen such that the numbers of molecules of the target and reference genomic sequences are identical in normal cells which have not undergone loss of heterozygosity. When comparing the quantities of two genomic sequences in a sample, the enumerative methods are useful to identify a statistically-significant difference between the two quantities, and to correlate any difference, to a degree of defined statistical confidence, with the presence in the sample of a subpopulation of cells having an altered (e.g. loss of heterozygosity) genomic sequence.

In a preferred embodiment, enumerative detection of a nucleic acid is accomplished by exposing a nucleic acid sample to first and second complementary oligonucleotides comprising a detectable label. Any detectable label may be used. Preferred labels include mass labels, electromagnetic labels, fluorescent labels, enzymatic labels, photo-emitting labels, and other labels known in the art. A first oligonucleotide is capable of hybridizing to a genetic region suspected to be mutated in cancer or precancer cells. A second oligonucleotide is capable of hybridizing to a region known not to be mutated in cancer or precancer cells. After washing to remove unhybridized oligonucleotides, the number of each of first and second oligonucleotides is counted. A statistically-significant difference between the number of first and second oligonucleotides is indicative of a mutation in a subpopulation of nucleic acids in the sample.

In preferred methods of the invention, first and second oligonucleotides are radionucleotides, and are isolated from other sample components by, for example, gel electrophoresis, chromatography, and mass spectrometry. Also in a preferred embodiment, either or both of the first and second radionucleotides is a chain terminator nucleotide, such as a dideoxy nucleotide. A preferred radionucleotide for use in methods of the invention is selected from the group consisting of $^{32}P$, $^{33}P$, $^{35}S$, $^{3}H$, $^{125}I$, and $^{14}C$. The number of first and second radionucleotides may be determined by counting. Methods of the invention are especially useful for the detection of massive nucleotide deletions, such as those that occur in loss of heterozygosity.

A massive loss of genetic material is detected as a reduction in the expected number in a sample of a nucleic acid fragment that is chosen to represent a genomic region suspected to be lost. For example, deletion of regions including all or part of human chromosome 18q have been associated with the development of cancer. According to the invention, a reduction in the number of cells in a sample having an intact 18q region is determined by comparing the number of a portion of the 18q region detected in the sample to the number of that region expected to occur in the sample. Similarly, a point mutation is detected by methods of the invention as a reduction in the sample of the number of wild-type nucleic acids encompassing the nucleotide suspected to be mutated. Accordingly, methods of the invention detect a mutation by detecting a reduction in the number of a nucleic acid expected to be in a sample. As described in detail below, methods of the invention are useful to detect a mutation in a heterogeneous cellular population without requiring the detection of multiple mutations.

An additional feature of the invention is that it has now been recognized that materials from cells lining the colon (e.g., a polyp or lesion) are shed onto forming stool only in a region comprising a longitudinal stripe along the length of the stool. Thus, unless the stool sample under investigation is a whole stool or comprises at least a cross-section of a stool, the sample will contain the relevant diagnostic information only by chance. The colon contains numerous bends and folds throughout its length. See, U.S. Pat. No. 5,741,650. Epithelial cells lining the colon normally migrate from a basal position in colonic crypts, where stem cells divide by mitosis, to the top of the crypts and are then shed into the lumen. Colonic epithelial cells that line the intestinal lumen typically undergo regeneration every four to five days as a result of the rapid turnover rate through the epithelium. Accordingly, sloughed epithelial cells or their DNA are constantly being deposited in the forming stool as it passes through the lumen. As the stool proceeds toward the rectum and becomes progressively more solid (from an initial liquid state), epithelial cells are only sloughed onto the portion of the stool making contact with the portion of the lumen that formerly contained those cells in its epithelial lining. Epithelial cells of a polyp undergo the same rapid life cycle and shedding described above for normal colonic epithelial cells. Accordingly, cells shed from polyps are typically only absorbed onto the surface of the forming stool that makes contact with the polyp. However, if the stool is in a liquid state, mixing of shed polyp cells throughout the stool occurs automatically.

Accordingly, the present invention provides methods for detecting genomic changes in a subpopulation of cells in a sample of biological material. In a particularly preferred embodiment, the sample comprises tissue and/or body fluid from members of a population. Pooled samples are useful to screen large numbers of individuals, to identify genomic features (e.g., mutations, single nucleotide polymorphisms), indicative or associated with a disease, or in pharmacogenomic, or pharmacogenetic applications. Methods of the invention are useful for the detection of changes in the nucleotide sequence of an allele in a small subpopulation of cells present in a large, heterogeneous sample of diagnostically-irrelevant biological material.

Also, in a preferred embodiment, transformed cells sought to be detected using methods according to the invention are malignant cells. Transformed cells detected according to methods of the invention may be induced transformants, transformed, for example, by a virus, by radiation, or by chemical or other carcinogenic means. Methods of the invention may be performed on any biological sample, including tissue and body fluid samples. Particularly preferred biological samples include pus, transudates, sputum, semen, blood, saliva, milk, cerebrospinal fluid, ascitic fluid, and urine. In an important embodiment of the invention, the sample is stool which is analyzed to detect colorectal cancer or precancer. Methods of the invention may be practiced by exposing a biological sample obtained from individual or pooled samples to one or more detectably-labeled nucleotides in order to separately detect the number X of a first polynucleotide and the number Y of a second polynucleotide.

In a preferred embodiment the first and second radiolabeled oligonucleotides are separable from each other. For example, the first and second oligonucleotides are of different sizes and can be separated by gel electrophoresis, chromatography or mass spectrometry. In one embodiment the first and second oligonucleotides are of different lengths. In a preferred embodiment the size difference is imparted by a size marker which is specifically attached to one of the two oligonucleotides. Alternatively a different size marker is attached to each oligonucleotide. After separation, the number of radioactive decay events is measured for each oligonucleotide, and the number of molecules is calculated as described herein.

In a more preferred embodiment, the first and second oligonucleotides are of the same size but are labeled with different detectable labels.

Methods of the invention are especially useful for the detection of colorectal cancer or precancerous cells in humans. In a preferred embodiment, methods of the invention are useful for the detection of colorectal cancer or precancerous cells in a patient population. For purposes of the present invention, precancerous cells are cells that have a mutation that is associated with cancer, and which renders such cells susceptible to becoming cancerous. Such methods comprise determining whether cells or nucleotide debris in a stool sample include a deletion of a polynucleotide normally present in a wild-type genome of the human or other mammal. The sample may be exposed to a plurality of first and second oligonucleotide probes under hybridization conditions, thereby to hybridize (i) first probe to copies of a first polynucleotide segment characteristic of a wild-type genomic region known or suspected not to be deleted in cells of the sample and (ii) second probe to copies of a second polynucleotide segment characteristic of the wild-type genomic region suspected of being mutated in the sample. The number of duplexes formed with each of the first and second probes is then detected and counted. The presence of a statistically-significant difference in those two numbers is indicative of the presence in the sample of a mutation that may be characteristic of colorectal cancer. Endoscopy or other visual examination procedures are then indicated.

Methods according to the invention also may be used to detect a loss of heterozygosity at an allele by determination of the amounts of maternal and paternal alleles comprising a genetic locus that includes at least one single-base polymorphism. A statistically-significant difference in the numbers of each allele is indicative of a mutation in an allelic region encompassing the single-base polymorphism. In this method, a region of an allele comprising a single-base polymorphism is identified, using, for example, a database, such as GenBank, or by other means known in the art. Probes are designed to hybridize to corresponding regions on both paternal and maternal alleles immediately 3' to the single base polymorphism. After hybridization, a mixture of at least two of the four common dideoxy nucleotides are added to the sample, each labeled with a different detectable label. A DNA polymerase is also added. Using allelic DNA adjacent the polymorphic nucleotide as a template, hybridized probe is extended by the addition of a single dideoxynucleotide that is the binding partner for the polymorphic nucleotide. After washing to remove unincorporated dideoxynucleotides, the dideoxynucleotides which have been incorporated into the probe extension are detected by determining the number of bound extended probes bearing each of the two dideoxy nucleotides in, for example, a scintillation counter. The presence of an almost equal number of two different labels mean that there is normal heterozygosity at the polymorphic nucleotide. The presence of a statistically-significant difference between the detected numbers of the two labels means that a deletion of the region encompassing the polymorphic nucleotide has occurred in one of the alleles.

Methods of the invention may be used to determine whether a patient is a candidate for follow-up invasive diagnostic or other procedures, such as endoscopy. For example, methods of the invention may be used to detect a mutation in a tumor suppressor gene or an oncogene in a subpopulation of cells in a stool sample obtained from a patient or in a pooled stool sample obtained from a patient population. An endoscopy procedure may then be performed on patients identified as having a mutation. A positive endoscopy result is then followed by polypectomy, surgery, or other treatment, as indicated, to remove cancerous or precancerous tissue.

In a particularly preferred embodiment, the method of the invention may detect, for example, the presence of a mutation in a specific tumor suppressor gene or oncogene in a population of patients by steps comprising collecting a biological specimen from members of the patient population, pooling the specimens to form a pooled sample, and analyzing the pooled sample by methods described above to detect a target mutation. Methods of the invention also include identifying genomic loci that are affected by or that affect the action of a drug.

Methods of the invention also utilize non-enumerative means for detection of nucleic acid mutations. Such methods utilize comparative, "bulk" detection, such as fluorescence, mass, or radionucleotides detected by bulk detection means—such as a scintillation counter. Such bulk detection methods are used to determine statistically significant differences between relative proportions of label associated with mild-type and mutant nucleic acids.

Accordingly, it is an object of the invention to provide methods for detecting loss of heterozygosity in a subpopulation of cells in a cellular sample. It is a further object of the invention to provide methods for detecting a genomic change in a subpopulation of cells, wherein the genomic change is indicative of cancer. It is another object of the invention to detect a loss of heterozygosity in a genomic region associated with cancer, such as a tumor suppressor region. It is yet another object of the invention to provide methods for detecting heterozygosity and the loss thereof at single-base polymorphic nucleic acids. Finally, it is an object of the invention to provide methods for the detection of cancer, and particularly colorectal cancer by detection of cells or cellular debris indicative of cancer in a heterogeneous sample, such as a stool sample. It is a further object of the invention to provide methods for the detection of cancer, and particularly colorectal cancer, in a population of humans, by detection of cells or cellular debris indicative of cancer in a heterogeneous sample, such as pooled samples.

Further aspects of the invention will become apparent upon consideration of the following detailed description and of the drawings.

DETAILED DESCRIPTION OF THE INVENTION

Figure 1:
FIG. 1 depicts differential primer extension as exemplified below.
Figure 1:
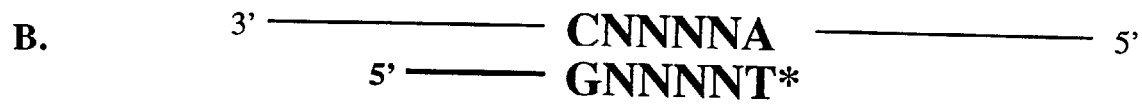

Methods according to the present invention are useful for the detection of loss of heterozygosity in a heterogeneous cellular sample in which the loss of heterozygosity occurs in only a small subpopulation of cells in the sample. Using traditional detection methods, such a subpopulation would be difficult, if not impossible, to detect especially if the deletion end points are unknown at the time of detection or a clonally-impure cellular population is used. See, e.g., U.S. Pat. No. 5,527,676 (reporting that a clonal population of cells should be used in order to detect a deletion in a p53 gene). Traditional methods for detection of mutations involved in carcinogenesis rely upon the use of a clonally-pure population of cells and such methods are best at detecting mutations that occur at known "hot spots" in oncogenes, such as k-ras. See, Sidransky, supra.

Methods of the present invention are useful for detecting loss of heterozygosity in a small number of cells in an impure cellular population because such methods do not rely upon knowing the precise deletion end-points and such methods are not affected by the presence in the sample of heterogeneous DNA. For example, in loss of heterozygosity, deletions occur over large portions of the genome and entire chromosome arms may be missing. Methods of the invention comprise counting a number of molecules of a target nucleic acid suspected of being deleted and comparing it to a reference number. In a preferred embodiment the reference number is the number of molecules of a nucleic acid suspected of not being deleted in the same sample. All that one needs to know is at least a portion of the sequence of a target nucleic acid suspected of being deleted and at least a portion of the sequence of a reference nucleic acid suspected of not being deleted. Methods of the invention, while amenable to multiple mutation detection, do not require multiple mutation detection in order to detect indicia of cancer in a heterogeneous sample.

Accordingly, methods of the present invention are useful for the detection of loss of heterozygosity in a subpopulation of cells or debris therefrom in a sample. Loss of heterozygosity generally occurs as a deletion of at least one wild-type allelic sequence in a subpopulation of cells. In the case of a tumor suppressor gene, the deletion typically takes the form of a massive deletion characteristic of loss of heterozygosity. Often, as in the case of certain forms of cancer, disease-causing deletions initially occur in a single cell which then produces a small subpopulation of mutant cells. By the time clinical manifestations of the mutation are detected, the disease may have progressed to an incurable stage. Methods of the invention allow detection of a deletion when it exists as only a small percentage of the total cells or cellular debris in a sample.

In a preferred embodiment, methods of the invention comprise a comparison of the number of molecules of two nucleic acids that are expected to be present in the sample in equal numbers in normal (non-mutated) cells. In a preferred embodiment, the comparison is between (1) an amount of a genomic polynucleotide segment that is known or suspected not to be mutated in cells of the sample (the "reference") and (2) an amount of a wild-type (non-mutated) genomic polynucleotide segment suspected of being mutated in a subpopulation of cells in the sample (the "target"). A statistically-significant difference between the amounts of the two genomic polynucleotide segments indicates that a mutation has occurred.

In a preferred embodiment, the reference and target nucleic acids are alleles of the same genetic locus. Alleles are useful in methods of the invention if there is a sequence difference which distinguishes one allele from the other. In a preferred embodiment, the genetic locus is on or near a tumor suppressor gene. Loss of heterozygosity can result in loss of either allele, therefore either allele can serve as the reference allele. The important information is the presence or absence of a statistically significant difference between the number of molecules of each allele in the sample. Also in a preferred embodiment, the reference and target nucleic acids are different genetic loci, for example different genes. In a preferred embodiment, the reference nucleic acid comprises both alleles of a reference genetic locus and the target nucleic acid comprises both alleles of a target genetic locus, for example a tumor suppressor gene. Specifically, in the case of a deletion in a tumor suppressor gene, the detected amount of the reference gene is significantly greater than the detected amount of the target gene. If a target sequence is amplified, as in the case of certain oncogene mutations, the detected amount of target is greater than the detected amount of the reference gene by a statistically-significant margin.

Methods according to the art generally require the use of numerous probes, usually in the form of PCR primers and/or hybridization probes, in order to detect a deletion or a point mutation. However, because methods of the present invention involve enumerative detection of nucleotide sequences and enumerative comparisons between sequences that are known to be stable and those that are suspected of being unstable, only a few probes must be used in order to accurately assess cancer risk. In fact, a single set (pair) of probes is all that is necessary to detect a single large deletion. The risk of cancer is indicated by the presence of a mutation in a genetic region known or suspected to be involved in oncogenesis. Patients or members of a patient population identified as being at risk based upon tests conducted according to methods of the invention are then directed to other, typically invasive, procedures for confirmation and/or treatment of the disease.

Enumerative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistically-significance between numbers of target and reference genes obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of mutant alleles in a sample containing mutant alleles (assumed herein to be at least 1%) and the further assumption that normal samples contain no mutant alleles. It is also assumed that a threshold differences between the numbers of reference and target genes must be at least 0.5% for a diagnosis that there is a mutation present in a subpopulation of cells in the sample. Based upon the foregoing assumptions, it is possible to determine how large N must be so that a detected difference between numbers of mutant and reference alleles of less than 0.5% is truly a negative (i.e. no mutant subpopulation in the sample) result 99.9% of the time.

Figure 2A:
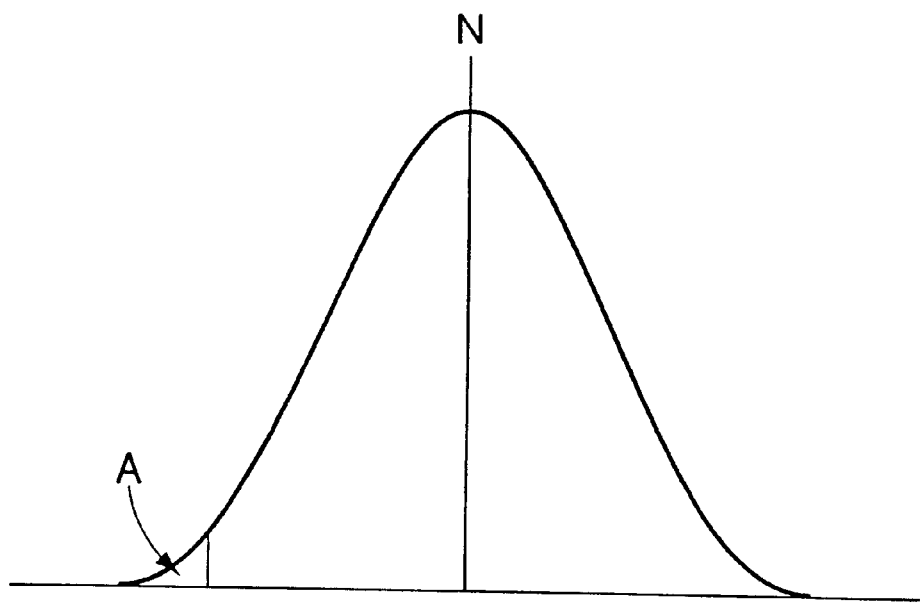
FIGS. 2A and 2B are model Gaussian distributions showing regions of low statistical probability.
Figure 2B:
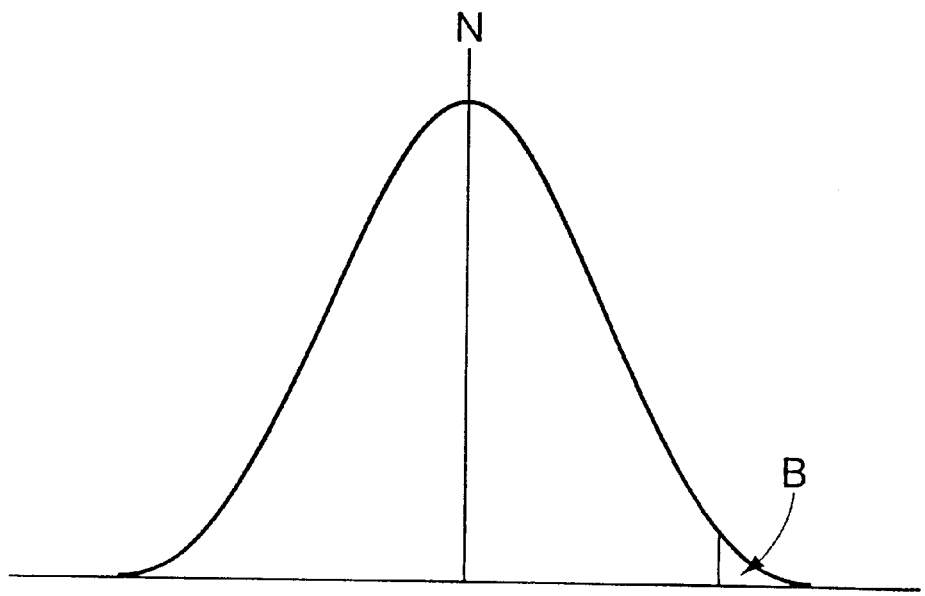

The calculation of N for specificity, then, is based upon the probability of one sample measurement being in the portion of the Gaussian distribution covering the lowest 3.16% of the population (the area marked "A" in FIG. 2A) and the probability that the other sample measurement is in the portion of the Gaussian distribution covering the highest 3.16% of the population (the area marked "B" in FIG. 2B). Since the two sample measurements are independent events, the probability of both events occurring simultaneously in a single sample is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N is set equal to 3.72 sigma. Since sigma (the standard deviation) is equal to $\sqrt{N}$, the equation may be solved for N as 553,536. This means that if the lower of the two numbers representing reference and target is at least 553,536 and if the patient is truly normal, the difference between the numbers will be less than 0.5% about 99.9% of the time.

Figure 3:
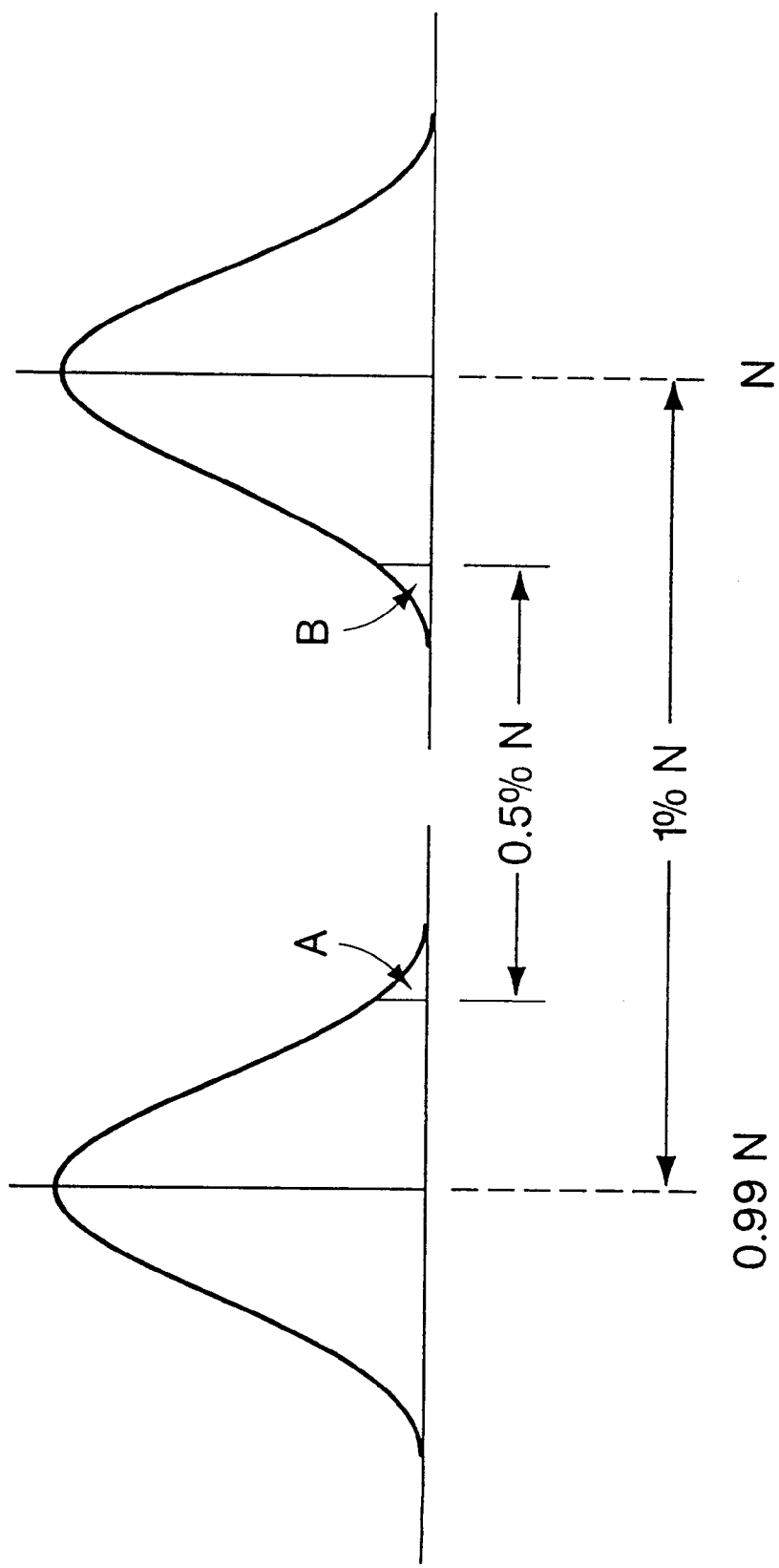
FIG. 3 is graph showing the probable values of N for a heterogeneous population of cells in which 1% of the cells are mutated.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 3 or in the area marked "B" in FIG. 3. If the two population means are a total of 1% different and if there must be a 0.5% difference between the number of target and reference genes, then the distance from either mean to the threshold for statistical significance is equivalent to 0.25% N (See FIG. 3) for 99% sensitivity. As shown in FIG. 3, 0.25% N corresponds to about 40% of one side of the Gaussian distribution. Statistical tables reveal that 40% of the Gaussian distribution corresponds to 1.28 standard deviations from the mean. Therefore, 1.28 sigma is equal to 0.0025N, and N equals 262,144. Thus, for abnormal samples, the difference will exceed 0.5% at least 99% of the time if the lower of the two numbers is at least 262, 144. Conversely, an erroneous negative diagnosis will be made only 1% of the time under these conditions.

In order to have both 99.9% specificity (avoidance of false positives) and 99% sensitivity (avoidance of false negatives), a sample with DNA derived from at least 553,536 (or roughly greater than 550,000) cells should be counted. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

Based upon the foregoing explanation, the skilled artisan appreciates that methods of the invention are useful to detect mutations in a subpopulation of a polynucleotides in any biological sample. For example, methods disclosed herein may be used to detect allelic loss (the loss of heterozygosity) associated with diseases such as cancer. Additionally, methods of the invention may be used to detect a deletion or a base substitution mutation causative of a metabolic error, such as complete or partial loss of enzyme activity. For purposes of exemplification, the following provides details of the use of methods according to the present invention in colon cancer detection. Inventive methods are especially useful in the early detection of a mutation (and especially a large deletion typical of loss of heterozygosity) in a tumor suppressor gene. Accordingly, while exemplified in the following manner, the invention is not so limited and the skilled artisan will appreciate its wide range of applicability upon consideration thereof.

Methods according to the invention preferably comprise comparing a number of a target polynucleotide known or suspected to be mutated to a number of a reference polynucleotide known or suspected not to be mutated. In addition to the alternative embodiments using either alleles or genetic loci as reference and target nucleic acids, the invention comprises a comparison of a microsatellite repeat region in a normal allele with the corresponding microsatellite region in an allele known or suspected to be mutated. Exemplary detection means of the invention comprise determining whether a difference exists between the number of counts of each nucleic acid being measured. The presence of a statistically-significant difference is indicative that a mutation has occurred in one of the nucleic acids being measured.

I. Preparation of a Stool Sample

A sample prepared from stool voided by a patient should comprise at least a cross-section of the voided stool. As noted above, stool is not homogenous with respect to sloughed cells. As stool passes through the colon, it absorbs sloughed cells from regions of the colonic epithelium with which it makes contacts. Thus, sloughed cells from a polyp are absorbed on only one surface of the forming stool (except near the cecum where stool is still liquid and is homogenized by intestinal peristalsis). Taking a representative sample of stool (i.e., at least a cross-section) and homogenizing it ensures that sloughed cells from all epithelial surfaces of the colon will be present for analysis in the processed stool sample. Stool is voided into a receptacle that is preferably small enough to be transported to a testing facility. The receptacle may be fitted to a conventional toilet such that the receptacle accepts stool voided in a conventional manner. The receptacle may comprise a mesh or a screen of sufficient size and placement such that stool is retained while urine is allowed to pass through the mesh or screen and into the toilet. The receptacle may additionally comprise means for homogenizing voided stool. Moreover, the receptacle may comprise means for introducing homogenization buffer or one or more preservatives, such as alcohol or a high salt concentration solution, in order to neutralize bacteria present in the stool sample and to inhibit degradation of DNA.

The receptacle, whether adapted to fit a toilet or simply adapted for receiving the voided stool sample, preferably has sealing means sufficient to contain the voided stool sample and any solution added thereto and to prevent the emanation of odors. The receptacle may have a support frame which is placed directly over a toilet bowl. The support frame has attached thereto an articulating cover which may be placed in a raised position, for depositing of sample or a closed position (not shown) for sealing voided stool within the receptacle. The support frame additionally has a central opening traversing from a top surface through to a bottom surface of the support frame. The bottom surface directly communicates with a top surface of the toilet. Extending from the bottom surface of the support frame and encompassing the entire circumference of the central opening is a means for capturing voided stool. The means for capturing voided stool may be fixedly attached to the support frame or may be removably attached for removal subsequent to deposition of stool.

Once obtained, the stool sample is homogenized in an appropriate buffer, such as phosphate buffered saline or a chaotropic salt solution. Homogenization means and materials for homogenization are generally known in the art. See, e.g., U.S. Pat. No. 4,101,279. Thus, particular homogenization methods may be selected by the skilled artisan. Methods for further processing and analysis of a biological sample, such as a stool sample are presented below.

II. Methods for Detection of Colon Cancer or Precancer

For exemplification, methods of the invention are used to detect a deletion or other mutation in or near the p53 tumor suppressor gene in cells obtained from a stool sample in a pooled sample. The p53 gene is a good choice because the loss of heterozygosity in p53 is often associated with colorectal cancer. An mRNA sequence corresponding to the DNA coding region for p53 is reported as GenBank Accession No. M92424. The skilled artisan understands that methods described herein may be used to detect mutations in any gene and that detection of a p53 deletion is exemplary of such methods. In the detection of loss of heterozygosity, it is not necessary to target any particular gene due to the massive deletions associated with this event. Accordingly, an LOH-type deletion involving, for example, p53 may be detected by probing a region outside, but near, p53 because that region is also likely to be deleted. At least a cross-section of a voided stool sample is obtained and prepared as described above. DNA or RNA may optionally be isolated from the sample according to methods known in the art. See, Smith-Ravin, et al., *Gut,* 36: 81–86 (1995), incorporated by reference herein. Methods of the invention may also comprise the step of amplifying DNA or RNA sequences using the polymerase chain reaction. However, methods of the invention may be performed on unprocessed stool.

Nucleic acids may be sheared or cut into small fragments by, for example, restriction digestion. The size of nucleic acid fragments produced is not critical, subject to the limitations described below. A target nucleic acid that is suspected of being mutated (p53 in this example) and a reference nucleic acid are chosen. The target and reference nucleic acids may be alleles on or near the p53 gene. Alternatively, the target nucleic acid comprises both alleles on or near the p53 gene and the reference nucleic acid comprises both alleles on or near a genetic locus suspected not to be deleted. Single-stranded nucleic acid fragments may be prepared using well-known methods. See, e.g., Sambrook, et al., *Molecular Cloning, A Laboratory Manual* (1989) incorporated by reference herein.

Either portions of a coding strand or its complement may be detected in methods according to the invention. In a preferred embodiment, both first and second strands of an allele are present in a sample during hybridization to an oligonucleotide probe. The sample is exposed to an excess of probe that is complementary to a portion of the first strand, under conditions to promote specific hybridization of the probe to the portion of the first strand. In a most preferred embodiment, the probe is in sufficient excess to bind all the portion of the first strand, and to prevent reannealing of the first strand to the second strand of the allele. Also in a preferred embodiment, the second strand of an allele is removed from a sample prior to hybridization to an oligonucleotide probe that is complementary to a portion of the first strand of the allele. For exemplification, detection of the coding strand of p53 and reference allele are described. Complement to both p53 and reference allele are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See Sambrook, Supra. As an alternative, isolation beads may be used to exclude complement as discussed in detail below.

After removal of complement, the target and reference nucleic acids are exposed to labeled nucleotides (e.g. probes) under conditions which promote specific association of the labeled nucleotides with the target and reference nucleic acids in a sample. In order to count the number of molecules of the target and reference nucleic acids, the label associated with the target nucleic acid must be distinguished from the label associated with the reference nucleic acid. In addition, label that is specifically associated with either target or reference nucleic acid must be distinguished from label that is not associated with either nucleic acid. The number of molecules of target nucleic acid is counted by measuring a number X of the label (e.g., radioactive decay events by measuring the total number of counts during a defined interval or by measuring the time it takes to obtain a predetermined number of counts) to enumerate the target nucleic acid.

According to methods of the invention, it is important to count the number of molecules in order to provide a statistical analysis of the likelihood of loss of heterozygosity. Comparison of the number of a detectable label without knowing the numbers of molecules associated with the label does not provide statistical data on the significance of any observed difference.

In a preferred embodiment, a detectable label is associated with a specific oligonucleotide prior to exposure to the sample. In a most preferred embodiment, a label comprises a single detectable molecule (e.g., a single radionucleotide) per oligonucleotide molecule. The labeled oligonucleotide is designed to hybridize specifically to a target nucleic acid. In one embodiment the target nucleic acid is a specific allele of a polymorphic genetic locus, and the oligonucleotide is designed to be complementary to the allele at the site of polymorphism. One skilled in the art can perform hybridizations under conditions which promote specific hybridization of the oligonucleotide to the allele, without cross hybridizing to other alleles. Similarly, radiolabeled oligonucleotides are designed to specifically hybridize with the reference nucleic acid.

Also in a preferred embodiment, a radionucleotide is specifically incorporated into an oligonucleotide by primer extension, after exposing the oligonucleotide to the sample under conditions to promote specific hybridization of the oligonucleotide with the target nucleic acid. In a preferred embodiment the oligonucleotide is unlabeled, and the radionucleotide is a radiolabeled chain terminating nucleotide (e.g. a dideoxynucleotide). In a most preferred embodiment, the radionucleotide is the chain terminating nucleotide complementary to the nucleotide immediately 5' to the nucleotide that base pairs to the 3' nucleotide of the oligonucleotide when it is specifically hybridized to the target nucleic acid. In the embodiment where the target nucleic acid is an allele of a polymorphic genetic locus, the oligonucleotide is preferably designed such that the 3' nucleotide of the oligonucleotide base pairs with the nucleotide immediately 3' to the polymorphic residue. In a preferred embodiment, a radiolabeled terminating nucleotide that is complementary to the residue at the polymorphic site is incorporated on the 3' end of the specifically hybridized oligonucleotide by a primer extension reaction. Similarly, in a preferred embodiment, a radionucleotide is specifically associated with a reference nucleic acid by primer extension. Other methods for specifically associating a radioactive isotope with a target or reference nucleic acid (for example a radiolabeled sequence specific DNA binding protein) are also useful for the methods of the invention.

In a preferred embodiment, prior to counting the radioactive decay events, the radionucleotides specifically associated with target and reference nucleic acids are separated from the radionucleotides that are not specifically associated with either nucleic acid. Separation is performed as described herein, or using techniques known in the art. Other separation techniques are also useful for practice of the invention. Methods of the invention also comprise distinguishing the radio-label specifically associated with a target nucleic acid from the radio-label specifically associated with a reference nucleic acid. In a preferred embodiment the isotope associated with the target is different from the isotope associated with the receptor. Different isotopes useful to radio-label nucleotides include $^{35}$S, $^{32}$P, $^{33}$P, $^{125}$I, $^{3}$H, and $^{14}$C. In one embodiment, an oligonucleotide complementary to a target nucleic acid is labeled with a different isotope from an oligonucleotide complementary to a reference nucleic acid. In another embodiment, the chain terminating nucleotide associated with the target nucleic acid is different from the chain terminating nucleotide associated with the reference nucleic acid, and the two chain terminating nucleotides are labeled with different isotopes.

In a preferred embodiment, radionucleotides labeled with different isotopes are detected without separating the radionucleotide associated with the target nucleic acid from the radionucleotide associated with the reference nucleic acid. The different isotopes useful to the invention have different characteristic emission spectra. The presence of a first isotope does not prevent the measurement of radioactive decay events of a second isotope. In a more preferred embodiment, the labeled oligonucleotide associated with the target nucleic acid is the same size as the labeled oligonucleotide associated with the reference nucleic acid (the labeled oligonucleotides can be labeled prior to hybridization or by primer extension). The two differentially labeled oligonucleotides are electrophoresed on a gel, preferably a denaturing gel, and the gel is exposed to an imager that detects the radioactive decay events of both isotopes. In this embodiment the two isotopes are detected at the same position on the imager, because both oligonucleotides migrate to the same position on the gel. Detection at the same position on the imager reduces variation due to different detection efficiencies at different positions on the imager.

Also in a preferred embodiment, the radionucleotide associated with the target nucleic acid is separated from the radionucleotide associated with the reference nucleic acid prior to measuring radioactive decay events. In a preferred embodiment the separated radionucleotides are labeled with the same isotope.

Preferred separation methods comprise conferring different molecular weights to the radionucleotides specifically associated with the target and reference nucleic acids.

Also in a preferred embodiment, first probes comprise a "separation moiety." Such separation moiety is, for example, hapten, biotin, or digoxigenin. The separation moiety in first probes does not interfere with the first probe's ability to hybridize with template or be extended. In an alternative embodiment, the labeled ddNTPs comprise a separation moiety. In yet another alternative embodiment, both the first probes and the labeled ddNTPs comprise a separation moiety. Following the extension reaction, a high molecular weight molecule having affinity for the separation moiety (e.g., avidin, streptavidin, or anti-digoxigenin) is added to the reaction mixture under conditions which permit the high molecular weight molecule to bind to the separation moiety. The reaction components are then separated on the basis of molecular weight using techniques known in the art such as gel electrophoresis, chromatography, or mass spectroscopy. See, Ausubel et al., *Short Protocols in Molecular Biology*, 3rd ed. (John Wiley & Sons, Inc., 1995); Wu *Recombinant DNA Methodology II*, (Academic Press, 1995).

Also in a preferred embodiment the radionucleotide associated with a first allele of a polymorphic genetic locus is separated from the radionucleotide associated with a second allele of the polymorphic locus by differential primer extension, wherein the extension products of a given oligonucleotide primer are of a different length for each of the two alleles. In differential primer extension (exemplified in FIG. 1) an oligonucleotide is hybridized such that the 3' nucleotide of the oligonucleotide base pairs with the nucleotide that is immediately 5' of the polymorphic site. The extension reaction is performed in the presence of a radiolabeled terminator nucleotide complementary to the nucleotide at the polymorphic site of the first allele. The reaction also comprises non-labeled nucleotides complementary to the other 3 nucleotides. Extension of a primer hybridized to the first allele results in a product having only the terminator nucleotide incorporated (exemplified in FIG. 1A, T* is the labeled terminator nucleotide). Extension of a primer hybridized to the second allele results in a product that incorporates several non-labeled nucleotides immediately 5' to the terminator nucleotide (exemplified in FIG. 1B). The number of non-labeled nucleotides that are incorporated is determined by the position, on the template nucleic acid, of the closest 5' nucleotide complementary to the terminator nucleotide. In an alternative embodiment, differential primer extension comprises a labeled oligonucleotide and a non-labeled terminator nucleotide.

Labeled probes are exposed to sample under hybridization conditions. Such conditions are well-known in the art. See, e.g., Wallace, et al., *Nucleic Acids Res.*, 6:3543–3557 (1979), incorporated by reference herein. First and Second oligonucleotide probes that are distinctly labeled (i.e. with different radioactive isotopes, fluorescent means, or with beads of different size) are applied to a single aliquot of sample. After exposure of the probes to sample under hybridization conditions, sample is washed to remove any unhybridized probe. Thereafter, hybridized probes are detected separately for p53 hybrids and reference allele hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a difference between the amount of p53 detected and the amount of the reference allele detected greater than a 0.5% difference with at least 550,000 events (earlier shown to be the threshold of significance), it may be assumed that a mutation has occurred in the region involving p53 and a patient or at least one member of a patient population is at risk for developing or has developed colon cancer. Statistical significance may be determined by any known method. A preferred method is outlined above.

The determination of a p53 mutation allows a clinician to recommend further treatment, such as endoscopy procedures, in order to further diagnose and, if necessary, treat the patient's condition. The following examples illustrate methods of the invention that allow direct quantification of hybridization events.

III. Pharmacogenomic/Pharmacogenetic Application

In a preferred embodiment, pooled samples are analyzed according to methods of the invention to determine clinically-important genomic loci or variants. Identification of such loci or variants is important in drug development and in the design of prophylactic, therapeutic, diagnostic, safety, and efficacy protocols. For example, the mechanism of action of most drugs involves interaction of the drug with proteins and/or nucleic acids. Nucleic acid polymorphisms may have profound effects on the response exhibited by a patient to a drug. One genomic variant may result in over-production of a protein that causes adverse reaction to a drug that produces no adverse reaction in another patient with an alternate variant. Methods of the invention, therefore, are useful to identify genetic loci, especially single nucleotide polymorphic loci, that are affected by or alter the efficacy or safety of a pharmaceutical.

Once polymorphic loci that effect drug efficacy or safety are identified in the pooled sample, individual patients are analyzed to determine a treatment regimen that is compatible with the patient's pharmacogenomic makeup. For example, one or more polymorphic variants may be used to determine which of several possible treatments (e.g. drugs) should be administered for maximum therapeutic effect.

The analysis of polymorphic variants is also useful, with respect to drug efficacy or clearance, to determine the expected rate of drug metabolism in a patient or patient population. Whereas pooled samples may be used to determine overall drug efficacy in light of genomic variance, these studies also allow the development of "designer drugs" which are administered to patients based upon the patient's array of polymorphic variants.

What is claimed is:

1. A method for detecting the presence of a mutant DNA in a pooled biological sample, comprising the steps of:
    a) pooling biological samples collected from a plurality of members of a patient population;
    b) determining from said pooled samples a number X of a first wild-type polynucleotide characteristic of a genomic region of said members of said patient population that is not mutated in said subpopulation of transformed cells;
    c) determining from said pooled biological sample a number Y of a second wild-type polynucleotide in a genomic region of one or more members of said patient population suspected of being mutated in said subpopulation of transformed cells; and
    d) determining whether a difference exists between number X and Y, the presence of a statistically-significant difference being indicative of a clonal subpopulation of transformed cells in said pooled biological sample.

2. The method according to claim 1, wherein said mutant DNA induces cancer.

3. The method according to claim 1, wherein said pooled biological sample is selected from the group consisting of pus, transudates, sputum, semen, urine, blood, milk, saliva, cerebrospinal fluid, ascitic fluid, and biopsy tissue.

4. The method according to claim 1, wherein said pooled biological sample comprises a stool sample obtained from each member of a patient population.

5. The method according to claim 1, wherein step b) comprises exposing said pooled biological sample to a first oligonucleotide probe having a nucleotide sequence complementary to at least a portion of nucleotide sequence of said first polynucleotide.

6. The method according to claim 5, wherein said first oligonucleotide probe is detectably labeled.

7. The method according to claim 5, wherein said number x is proportional to the number of said first oligonucleotide probes that forms duplex with said first polynucleotide.

8. The method according to claim 1, wherein step c) comprises exposing said pooled biological sample to a second oligonucleotide probe having a nucleotide sequence complementary to at least a portion of said second polynucleotide.

9. The method according to claim 8, where said number y is proportional to a number of second oligonucleotide probes that forms duplex with said second oligonucleotide.

10. The method according to claim 8, wherein said second oligonucleotide probe is detectably labeled.

11. A method for detecting the presence of a colorectal cancer or precancerous lesion in pooled mammalian tissue or body fluid samples obtained from a patient population, comprising the steps of:
    a) pooling said tissue or said body fluid samples collected from a plurality of members of a patient population;
    b) exposing said pooled biological sample to a plurality of a first oligonucleotide probe and to a plurality of a second oligonucleotide probe under hybridization conditions, thereby to hybridize
        1) said first oligonucleotide probes to copies of a first polynucleotide segment characteristic of wild-type cells of said members of said population, and
        2) said second oligonucleotide probes to copies of a second polynucleotide segment characteristic of a wild-type genomic region suspected to be deleted or mutated in colorectal cancer cells;
    c) detecting a first number of duplexes formed between said first probe and said first segment and a second number of duplexes formed between said second probe and said second segment; and
    d) determining whether there is a difference between the number of duplexes formed between said first probe and said first segment and the number of duplexes formed between said second probe and said second segment, the presence of statistically-significant difference being indicative of the presence in said pooled biological sample of a colorectal cancer or precancerous lesion.

12. The method according to claim 11, wherein said first and second oligonucleotide probes each are coupled to a distinct detectable label.

13. The method according to claim 11, wherein said first oligonucleotide probes are attached to a first particle in a ratio of one first oligonucleotide probe to one particle and said second oligonucleotide probes are attached to a second particle detectably distinct from said first particle in a ratio of one second oligonucleotide probe to one second particle, wherein said detecting step comprises separating hybridized from unhybridized first and second oligonucleotide probes and subsequently passing hybridized first and second oligonucleotide probes through a detector to determine said first and second numbers.

14. The method of claim 13, wherein said first and second particles are of detectably different sizes.

15. The method according to claim 13, wherein said first and second particles are of detectably different colors.

16. The method according to claim 11, further comprising prior to step a) the steps of converting double-stranded DNA in said sample aliquot to single-stranded DNA and removing complement to said first and second polynucleotide segments.

17. The method according to claim 16, wherein said removing step comprises hybridizing said complement to a nucleic acid probe attached to a magnetic particle and subsequently removing said magnetic particle from the sample.

18. A method for detecting a nucleic acid sequence change in a target allele in a subpopulation of cells in a pooled biological sample compromising the steps of:
    a) pooling biological samples collected from a plurality of members of a patient population,
    b) determining
        (i) an amount of wild-type target allele in said aliquot, and
        (ii) an amount of a reference allele in said aliquot; and
    c) detecting a nucleic acid sequence change in the target allele in a subpopulation of cells in said aliquot as
a statistically significant difference in the amount of wild-type target allele and the amount of reference allele obtained in said determining step.

19. The method according to claim 18, wherein said determining step comprises exposing said biological sample to a first oligonucleotide probe which hybridizes with a portion of said wild-type allele and to a second oligonucleotide probe capable of hybridizing to a portion of said reference allele, and removing from said sample any unhybridized first or second oligonucleotide probe.

20. The method according to claim 18, wherein said pooled biological sample comprises stool obtained from each member of a patient population.

21. The method according to claim 18, wherein said target allele is a tumor suppressor allele.

22. The method according to claim 18, wherein said tumor suppressor allele is a p53 allele.

23. A method for detecting a change in the nucleotide sequence in a subpopulation of a target allele in a pooled heterogeneous sample of cellular material, comprising the steps of:
    a) pooling biological samples collected from a plurality of members of a patient population;
    b) exposing said pooled sample under hybridization conditions, to a plurality of isolation probes, each of which hybridizes to at least a portion of only one member selected from a first group consisting of a coding strand of said target allele and complement of a coding strand of said target allele;
    c) exposing the pooled sample, under hybridization conditions, to a plurality of second isolation probes, each of which hybridizes to at least a portion of only one member selected from a second group consisting of a coding strand of a reference allele and a complement of a coding strand of said reference allele;
    d) contacting said pooled sample under hybridization conditions, with a plurality of first hybridization probes, each of which hybridizes to at least a portion of the member of said first group to which said first isolation probe does not hybridize;
    e) contacting said pooled samples under hybridization conditions, with a plurality of second hybridization probes, each of which hybridizes with at least a portion of the member of said second group to which said first isolation probe does not hybridize;
    f) removing non-hybridizing first and second hybridization probes from said pooled sample;
    g) determining an amount of each of said first and second hybridization probes remaining in said pooled sample after said removing step; and
    h) detecting allelic loss in a subpopulation of target allele as a statistically-significant difference in the amount of said first hybridization probe and said second hybridization probe obtained in said determining step.

24. The method according to claim 23, wherein said first and second hybridization probes are differently labeled.

25. The method according to claims 23, wherein said first and second hybridization probes are attached to first and second hybridization beads, respectively, in a ratio of one probe to one bead.

26. The method according to claim 25, wherein said first hybridization beads are of a size distinct from said second hybridization beads.

27. The method according to claim 26, wherein said detecting step comprises passing said first and second hybridization beads through a Coulter counter.

28. The method according to claim 23, wherein said target allele is an allele, the mutation of which is associated with disease.

29. The method according to claim 28, wherein said disease is cancer.

30. The method according to claim 28, wherein said sample of cellular material is a pooled stool sample.

31. The method according to claim 30, further comprising the step of performing an endoscopy procedure on a member of said patient population in whose stool sample allelic loss is detected.

32. A method for detecting a deletion in polymorphic locus in a subpopulation of cells in a pooled biological sample, comprising the steps of:
    a) pooling biological samples collected from a plurality of members of a patient population;
    b) detecting an amount of maternal allele at a polymorphic locus in said pooled sample;
    c) detecting an amount of a paternal allele at the polymorphic locus in said pooled sample; and
    d) determining whether a statistically-significant difference exists between the amount of maternal allele and the amount of paternal allele at the polymorphic locus, the presence of a statistically-significant difference being indicative of a deletion at the polymorphic locus in a subpopulation of cells in said pooled biological sample obtained from a patient population.

33. The method according to claim 32, wherein said polymorphic locus is a single base polymorphism and is heterozygous between said maternal and paternal alleles.

34. The method according to claim 33, wherein said detecting steps comprise,
    a) hybridizing probe to a portion of said polymorphic locus on both maternal and paternal alleles that is immediately adjacent to said single-based polymorphism;
    b) exposing said pooled sample aliquot to a mixture of detectably-labeled dideoxy nucleotide triphosphates under conditions which allow appropriate binding of said dideoxy nucleotide triphosphates to said single-base polymorphism;
    c) washing said sample; and
    d) counting an amount of each detectably-labeled dideoxy nucleotide triphosphate remaining for the sample.

35. The method according to claim 34, wherein said detectable label is selected from the group consisting of radioisotopes, fluorescent compounds, colorimetric compounds, enzymatic compounds, and particles.

36. The method according to claim 32, wherein said pooled biological sample is selected from the group consisting of pus, transudates, blood, urine, sputum, semen, saliva, milk, cerebrospinal fluid, ascitic fluid, biopsy tissue, and stool.

37. The method according to claim 32, wherein said polymorphic locus is identified from a database of nucleotide sequences.

38. A method for detecting heterozygosity at a single-nucleotide polymorphic locus in a pooled biological sample, comprising the steps of:

a) pooling biological samples collected from a plurality of members of a patient population;

b) hybridizing probes to a sequence immediately adjacent to a single-based polymorphism;

c) exposing said pooled samples to a plurality of different labeled dideoxy nucleotides;

d) washing said sample;

g) determining which of said dideoxy nucleotides are incorporated into said probes; and e) detecting heterozygosity at the single-nucleotide polymorphic site as the detection of two dideoxy nucleotides having been incorporated into the probe.

* * * * *